(12) United States Patent
Dehler

(10) Patent No.: US 7,628,538 B2
(45) Date of Patent: Dec. 8, 2009

(54) METHOD AND APPARATUS FOR CALIBRATING AN X-RAY DIAGNOSTIC SYSTEM

(75) Inventor: Juergen Dehler, Forchheim (DE)

(73) Assignee: Ziehm Imaging GmbH, Nuremberg (DE)

( * ) Notice: Subject to any disclaimer, the term of this patent is extended or adjusted under 35 U.S.C. 154(b) by 0 days.

(21) Appl. No.: 12/114,666

(22) Filed: May 2, 2008

(65) Prior Publication Data
US 2008/0285725 A1     Nov. 20, 2008

(30) Foreign Application Priority Data
May 5, 2007   (DE)  .................. 10 2007 021 183

(51) Int. Cl.
*G01D 18/00* (2006.01)
(52) U.S. Cl. ...................... 378/207; 378/205
(58) Field of Classification Search ............ 378/205, 378/207
See application file for complete search history.

(56) References Cited
U.S. PATENT DOCUMENTS
2003/0219102 A1* 11/2003 Mitschke et al. ........... 378/207

2005/0281385 A1   12/2005 Johnson et al.
2006/0115054 A1    6/2006 Yatsenko et al.

FOREIGN PATENT DOCUMENTS
DE    197 03 556     8/1998
EP     1 990 004    11/2008

OTHER PUBLICATIONS
European Exam Report, EP 1 990 004, dated Sep. 5, 2008, 3 pages.

* cited by examiner

*Primary Examiner*—Hoon Song
(74) *Attorney, Agent, or Firm*—Knobbe, Martens, Olson & Bear LLP

(57) ABSTRACT

The subject matter of the present application relates to methods for calibrating an X-ray diagnostic system and apparatus for use in the calibration methods. In one embodiment, the apparatus includes a position detection system having an acquisition unit. An X-ray phantom is disposed near the acquisition unit in a known position and/or orientation relative to a coordinate system of the position detection system. The X-ray phantom may be detachably mounted on the acquisition unit.

4 Claims, 3 Drawing Sheets

METHOD AND APPARATUS FOR CALIBRATING AN X-RAY DIAGNOSTIC SYSTEM

CROSS-REFERENCE TO RELATED APPLICATIONS

This application claims the right of priority under 35 U.S.C. § 119(a)-(d) to German Patent Application No. DE 10 2007 021 183.1, filed May 5, 2007, the entire disclosure of which is hereby incorporated by reference herein and made part of this specification.

BACKGROUND

1. Field

The subject matter of the present application relates generally to methods for calibrating an X-ray diagnostic system and apparatus for use in calibration methods.

2. Description of the Related Art

Medical interventions involving living subjects are increasingly performed using navigation assistance provided by a navigation support system. In some navigation support systems, a surgical instrument is guided by means of a position detection system relative to a tissue region of the subject undergoing treatment. Navigation assistance is of particular interest in body regions that cannot be visually inspected by the surgeon, such as when the instrument is inserted into the interior of the subject. For this purpose, the instrument, for example, a catheter, is guided in a virtual 3D volume generated by means of an imaging method prior to or during surgery. For example, an X-ray diagnostic machine may be used to generate a series of 2D projection images having a known projection geometry, and the 2D images may be used to generate a 3D volume data set. The 3D volume data set is transmitted to the navigation system, which is equipped with a position detection system for detecting positions of the markers. For high-precision navigation, the coordinate system of the position detection system can be aligned and/or oriented with the coordinate system of the 3D volume data set in a process commonly known as "registration." In one example, the registration process uses a phantom, which includes X-ray positive markers and/or markers that are detectable by the position detection system in a fixed spatial relation to each other.

Some methods for improving the precision of a reconstructed 3D data set from the 2D X-ray projection images account for deviations of the projection geometry from the actual geometry of the imaging system. For example, mechanical flexure of the X-ray diagnostic machine may cause such deviations. Therefore, some X-ray diagnostic machines may be "calibrated" with special X-ray phantoms. In some cases, a calibration is performed only at certain times such as, for example, prior to shipment of the diagnostic machine from the factory, after a repair involving replacement of mechanical components of the machine, or prior to the start of an examination.

German Patent DE 102 02 091 A1 discloses a device and a method for determining a coordinate transformation using a phantom in which X-ray positive markers and markers that are detectable by a position detection system are disposed in fixed spatial relation to one another. During a scan to generate the 2D X-ray projection images, the coordinates of the X-ray positive markers are determined in the reconstructed 3D volume and transmitted to the position detection system and the navigation support system for calibration.

German Patent DE 100 47 382 C2 discloses an X-ray phantom that comprises markers that are detectable by a position detection system. Coordinates of the detected positions of the markers are measured in a coordinate system of the position detection system and in a coordinate system of the X-ray diagnostic system. The measured coordinates are used to calculate a coordinate transformation between these coordinate systems.

Many calibration methods using a position detection system suffer from disadvantages. For example, the positions of both the X-ray phantom and the X-ray beam receiver (or a part of the X-ray diagnostic system that is in a fixed spatial relation with the X-ray beam receiver according to a kinematic model) must be measured to calculate the coordinate transformation. Due to the inaccuracies of making at least two measurements, the coordinate transformation includes calculable error. For example, if the position detection system uses two cameras in fixed spatial relation to each other, the error in the coordinate system will increase as the angle between a point of the X-ray phantom or the X-ray diagnostic system and the two entrance pupils of the cameras gets smaller. In another example, if the position detection system includes an acquisition unit, the error in the coordinate system will increase as the distance between the acquisition unit and the X-ray phantom or the X-ray diagnostic system increases.

SUMMARY

Because of the foregoing (and other) challenges and limitations, there is a need to improve the accuracy of calibrations of an X-ray diagnostic system using a position detection system and an X-ray phantom. In various embodiments, methods and systems provide improved accuracy for determining the position of the X-ray phantom in the coordinate system of the X-ray diagnostic system. In certain embodiments, only the position of the X-ray beam receiver or a part of the X-ray diagnostic system is detected by the position detection system. The X-ray phantom may be disposed in a known position and/or orientation relative to and in the vicinity of an acquisition unit of the position detection system. The X-ray phantom may be detachably mounted on the acquisition unit. In some example calibration methods, the acquisition unit and the X-ray phantom are positioned in the path of rays of the X-ray diagnostic system so that a minimum of two X-ray projection images of the X-ray phantom can be taken and the position of the X-ray beam receiver or the X-ray diagnostic system can be detected for at least one projection geometry.

An embodiment of a calibration system for calibrating an X-ray diagnostic system is provided. The calibration system comprises an X-ray phantom and a position detection system for detecting a marker configuration. The calibration system is characterized in that the X-ray phantom is disposed in a position and orientation that is specified with respect to a coordinate system of the position detection system. The X-ray phantom may be disposed relative to and in the vicinity of an acquisition unit of the position detection system. The X-ray phantom may be mounted by a mount on the position detection system.

In certain embodiments, the calibration system is characterized in that the X-ray phantom is detachably and reproducibly mounted in an accurate position by means of a mount on the acquisition unit of the position detection system.

In certain embodiments, the calibration system is characterized in that the X-ray phantom is integrated into the acquisition unit of the position detection system.

In certain embodiments, the calibration system is characterized in that the acquisition unit of the position detection system comprises a single camera and at least one planar mirror disposed in the path of rays between the camera and the marker configuration. The camera has a field of view having a first area onto which the marker configuration is imaged along a direct ray and at least a second area in which the marker configuration is imaged along at least one ray that is reflected by the mirror.

Embodiments of a method of calibrating an X-ray diagnostic system are provided. The method comprises providing a position detection system for detecting a marker configuration. The position detection system comprises an acquisition unit and an X-ray phantom disposed on the acquisition unit. The method further comprises positioning the acquisition unit in a path of rays of the X-ray diagnostic system in a first projection geometry so that at least a portion of the X-ray phantom is projected onto an X-ray beam receiver by an X-ray source and so that the marker configuration can be detected by the position detection system. Preferably, the method further comprises acquiring a first 2D X-ray projection of the X-ray phantom and determining a position of the marker configuration with the position detection system in the first projection geometry. Preferably, the method further comprises acquiring a second 2D X-ray projection of the X-ray phantom in at least a second projection geometry and performing a 3D reconstruction of the X-ray phantom. Preferably, the method further comprises calculating a coordinate transformation between coordinate systems of the X-ray phantom and the X-ray diagnostic system based at least in part on the detected position of the X-ray phantom relative to the marker configuration and the position of the projection image of the X-ray phantom in the reconstructed volume relative to the marker configuration.

BRIEF DESCRIPTION OF THE DRAWINGS

The following drawings and the associated descriptions are provided to illustrate embodiments of the present disclosure and do not limit the scope of the claims.

DETAILED DESCRIPTION OF PREFERRED EMBODIMENTS

Figure 1:
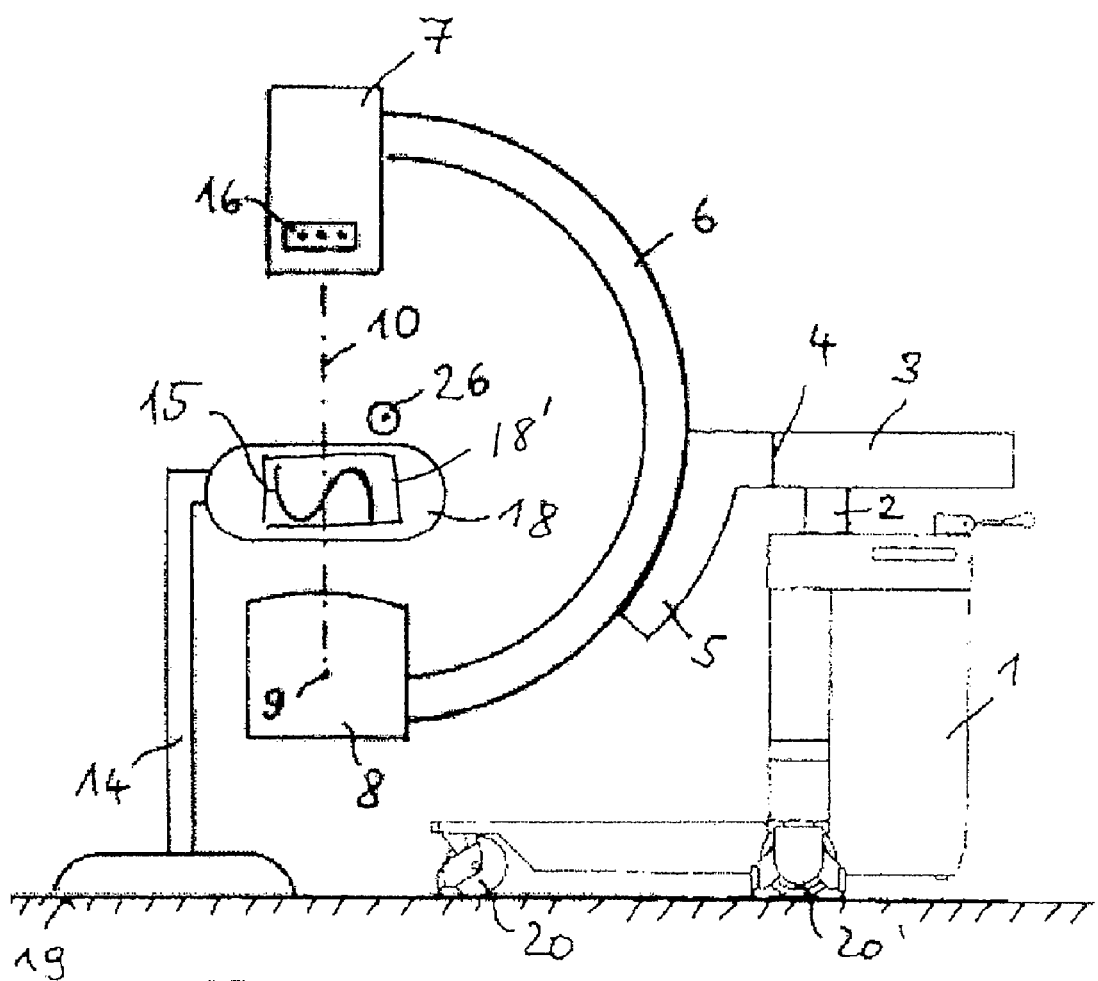
FIG. 1 schematically illustrates an embodiment of a mobile X-ray diagnostic system.

FIG. 1 schematically illustrates an embodiment of an X-ray diagnostic system. In this embodiment, the X-ray diagnostic system is mobile and comprises an instrument cart 1 that moves on rollers 20, 20' along the floor 19. The instrument cart 1 may be configured to support a C-shaped arm 6 ("C-arm"). The C-arm 6 may be adjustable in multiple ways. For example, the C-arm 6 may be slidably mounted along its circumference in an arm mount 5 so that the C-arm 6 can circumferentially move along about center 26 of the C-arm 6.

The arm mount 5 may be disposed on the instrument cart 1 so that it is multiply adjustable. For example, in some embodiments, the arm mount 5 is mounted with a pivot bearing 4 on a horizontally movable guide 3 so that it can pivot about a horizontal axis. The horizontal guide 3 is mounted on a column 2 so that it can be adjusted vertically and can be pivoted about the vertical axis of the column 2. In certain embodiments, some or all of the devices for adjusting the C-arm 6 are fitted with position measuring sensors, whose measurements can be transmitted to a central motion control unit 21 of the X-ray diagnostic system. In certain embodiments, some or all of the adjustment axes can be selectably locked, either individually or in combination, by brakes. In some implementations, the rollers 20, 20' have a locking brake. In certain embodiments, the C-arm 6 is configured to be adjustable along one or more directions or axes. For example, adjustment of the C-arm 6 may occur via the mount 5 (e.g., orbital movement through an angle $\alpha$), via the horizontal guide 3 (horizontal movement along a y-axis), and via the column 2 (height adjustment along a z-axis). Adjustment of the C-arm 6 can be implemented using electric motors arranged along some or all of the adjustable axes. The motors may be controlled by the central control unit 21 of the diagnostic system.

In some embodiments, an X-ray source 8 and an X-ray beam receiver 7 are disposed on opposing ends of the C-arm 6. When the X-ray source 8 is actuated, X-rays are emitted from a focal spot 9 and propagate to an entrance window 11 (shown in FIG. 4) of the X-ray beam receiver 7. In some embodiments of the X-ray beam receiver 7, the X-rays propagate as a cone-shaped or pyramid-shaped beam having a central ray 10. In some embodiments, the entrance window 11 is substantially rectangular.

As illustrated in FIG. 1, the X-ray diagnostic system may comprise a position detection system 18. In various embodiments, the position detection system 18 can be an optical system (e.g., an infrared system, a laser measuring system, a camera or stereo camera system) and/or a system based on measurement of a magnetic field and/or an electric field.

In certain embodiments, a marker configuration 16 is disposed in, on, or near the X-ray beam receiver 7. The position (and/or orientation) of the marker configuration 16 can be determined with the position detection system 18. For example, in some embodiments, the marker configuration 16 may comprise one or more markers that are detectable by the position detection system 18. In other embodiments, the marker configuration 16 comprises one or more spots that can be scanned with a pointer. The position and/or orientation of the spots may be determined by repeatedly scanning the spots with the pointer in the coordinate system of the position detection system 18.

In the embodiment schematically illustrated in FIG. 1, the system includes an X-ray phantom 15. In this embodiment, the X-ray phantom 15 is mounted in, on, or near an acquisition unit 18' of the position detection system 18. The acquisition unit 18' may be adjustably mounted on a stand 14. In certain embodiments, the X-ray phantom 15 comprises a single X-ray positive spot marker or an X-ray positive structure. Other types of X-ray phantoms 15 are used in other embodiments.

Figure 2:
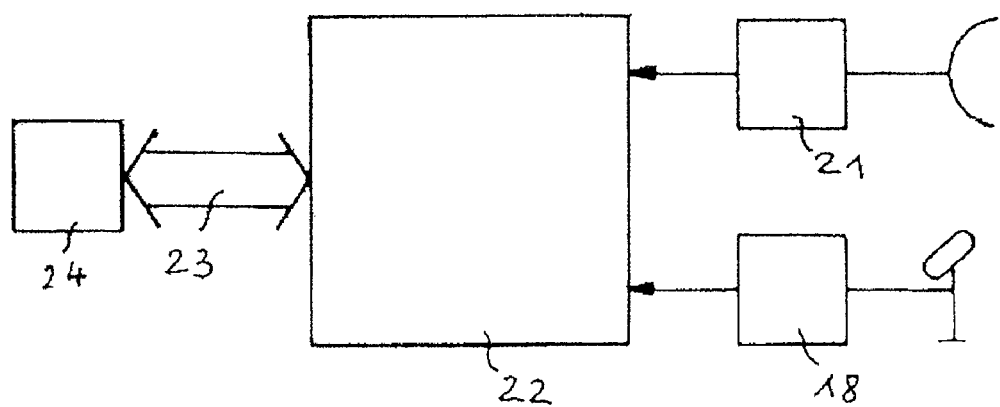
FIG. 2 is a schematic representation of an embodiment of a circuit arrangement for an X-ray diagnostic system comprising a position detection system.

FIG. 2 is a schematic representation of an embodiment of a circuit arrangement for an X-ray diagnostic system comprising a position detection system 18. In this embodiment, a control computer 21 controls some or all of the movements and X-ray procedures of the X-ray diagnostic system. The control computer 21 is operably connected to a central processor 22. In certain embodiments, the central processor 22 comprises some or all of the modules used to process and/or store the kinematic model of the X-ray diagnostic system, the acquired 2D projections, correction tables (e.g., look-up tables "LUTs") acquired during the calibration, and modules used to reconstruct a 3D volume from the 2D X-ray projections. The central processor 22 may also comprise a module for performing coordinate transformations. In other embodiments, some or all of these modules are remote from the central process 22 and communicate with the central processor 22 via wired and/or wireless techniques. The position detection system 18 may be configured to communicate with the central processor 22 (e.g., using wired and/or wireless techniques). In the circuit arrangement illustrated in FIG. 2, the central processor 22 communicates with a navigation module 24 via a data interface 23. The data interface 23 may comprise a wired and/or wireless communication interface. In certain embodiments, the position detection system 18 may communicate with the navigation module 24 via the data interface 23.

In certain embodiments of a method for calibrating an X-ray diagnostic system, the X-ray phantom 15 is disposed in, on, or near the position detection system 18. The stand 14 may be adjusted so that the X-ray phantom 15 is positioned in the path of the X-rays so that at least a portion of the X-ray phantom 15 intercepts the X-rays and is imaged by the X-ray beam receiver 7. The position detection system 18 also may be used to detect the position of the marker configuration 16. In certain embodiments of the calibration method, one 2D projection image of the X-ray phantom 15 (or a portion thereof) is acquired for at least two different projection geometries, and the position of the marker configuration 16 is determined for at least one projection geometry. In certain such embodiments, the calibration method includes calculating a coordinate transformation between the coordinate system of the X-ray phantom 15 and the coordinate system of the X-ray diagnostic system based at least in part on information including the measured position of the X-ray phantom 15 relative to the marker configuration 16, the known position of the marker configuration 16 in a coordinate system of the X-ray diagnostic system, and the determined position of the projection of the X-ray phantom 15 in the 2D X-ray projection images. In certain preferred embodiments, the calibration method is capable of calculating the coordinate transform based on detection of the position of the X-ray phantom 15 in a single position.

Figure 3:
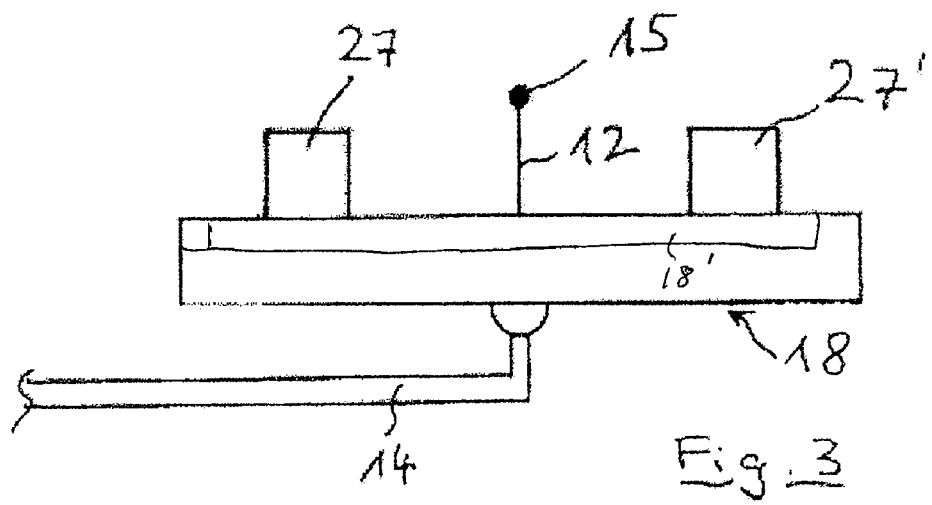
FIG. 3 schematically illustrates an embodiment of an X-ray phantom that is mounted on an acquisition unit of a position detection system.

FIG. 3 schematically illustrates an embodiment of an X-ray phantom 15, which may be attached with a mount 12 to the acquisition unit 18' of the position detection system 18. In this embodiment, the X-ray phantom 15 comprises a quasi-spot-shaped X-ray positive marker. In other embodiments, the X-ray phantom 15 may have a different shape. The mount 12 preferably is substantially X-ray transparent. In certain embodiments, the mount 12 is detachable from the acquisition 18' unit. The mount 12 advantageously may provide for reproducible positioning of the X-ray phantom 15. For example, in one embodiment, the mount 12 comprises a threaded connector that allows the mount to be screwed into (or out of) the acquisition unit 18'. In the embodiment illustrated in FIG. 3, the acquisition unit 18' of the position detection system 18 comprises two cameras 27, 27' of a stereo camera system. In some embodiments, the acquisition unit 18' is adjustably mounted on the stand 14.

Figure 4:
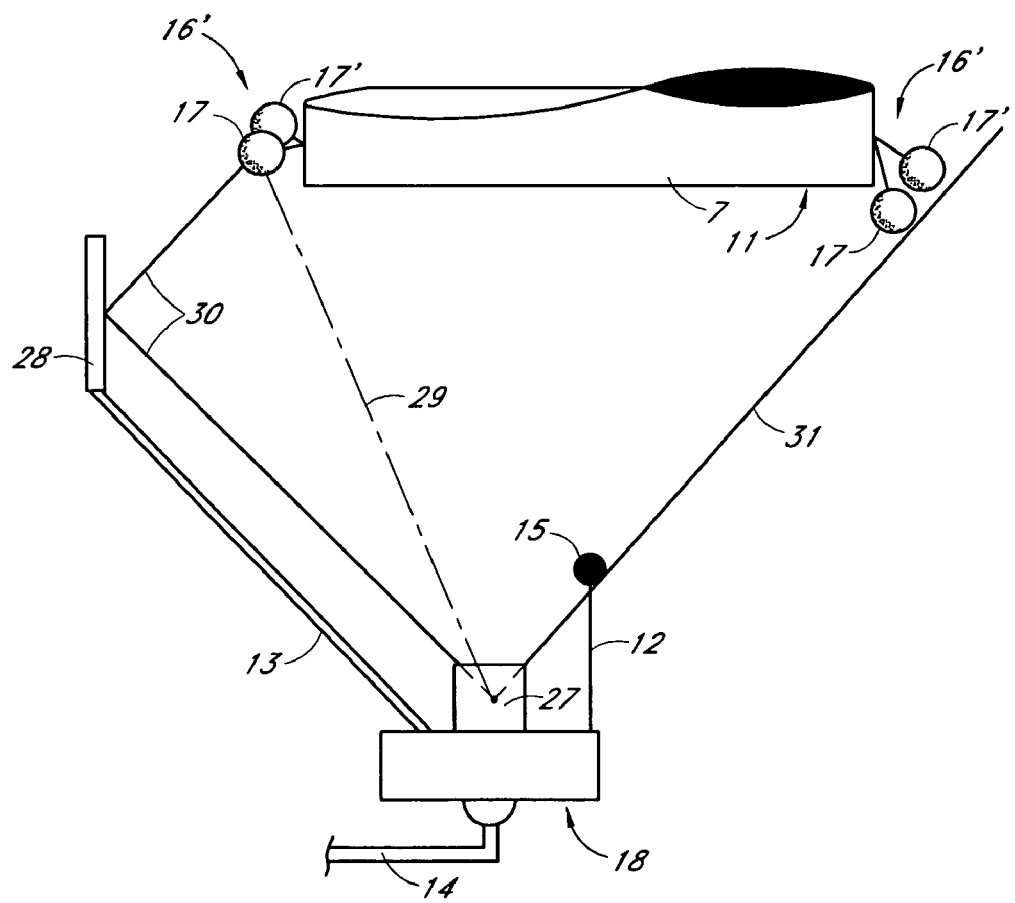
FIG. 4 schematically illustrates an embodiment of an X-ray phantom that is mounted with an X-ray transparent mount on a position detection system having a single camera.

FIG. 4 schematically illustrates an embodiment of the X-ray phantom 15 that is mounted on an acquisition unit of a position detection system 18 using a mount 12 that preferably is X-ray transparent. The acquisition unit may be adjustably mounted on the stand 14. The acquisition unit comprises a camera 27. In some embodiments, the camera 27 has a large angle of aperture that is limited by a limiting ray 31 schematically shown in FIG. 4. A planar mirror 28 is disposed on the acquisition unit with a mirror mount 13 so that the orientation of the planar mirror 28 with respect to the camera 27 is known. In the illustrated embodiment, the marker configuration 16, 16' disposed adjacent the X-ray beam receiver 7 comprises marker 17, 17'. Preferably, the planar mirror 28 is positioned so that at least some of the markers 17, 17' can be detected by the camera 27 along a direct ray 29 and along a reflected ray 30. A possible advantage of the position detection system 18 shown in FIG. 4 is that it provides an inexpensive system in which a single camera 27 is used for determining the position of the X-ray phantom 15 relative to the markers 17, 17' of the marker configuration 16, 16'.

Although described herein in the context of an X-ray diagnostic system, a person of ordinary skill will recognize that embodiments disclosed herein may be used with other medical devices. Methods and processes described herein may be embodied in, and partially or fully automated via, software code modules executed by one or more general and/or special purpose computers. The word "module" refers to logic embodied in hardware and/or firmware, or to a collection of software instructions written in a programming language. Software code modules may be stored on any suitable type of computer-readable medium. In any method or process disclosed herein, the acts or operations of the method or process may be performed in any suitable sequence and are not necessarily limited to any particular disclosed sequence. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Reference throughout this specification to "some embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner in one or more embodiments, as would be apparent to one of ordinary skill in the art from this disclosure. Additionally, although described in the illustrative context of certain preferred embodiments and examples, it will be understood by those skilled in the art that the disclosure extends beyond the specifically described embodiments to other alternative embodiments and/or uses and obvious modifications and equivalents. Thus, it is intended that the scope of the claims which follow should not be limited by the particular embodiments described above.

What is claimed is:

1. A system for calibrating an X-ray diagnostic system, the system comprising an X-ray phantom and a position detection system for detecting a marker configuration, the system characterized in that the X-ray phantom is disposed in a position and orientation that is specified with respect to a coordinate system of the position detection system, the X-ray phantom disposed relative to and in the vicinity of an acquisition unit of the position detection system, the X-ray phantom mounted by a mount on the position detection system, wherein said system is characterized in that the acquisition unit of the position detection system comprises a single camera and at least one planar mirror disposed in the path of rays between the camera and the marker configuration, the camera having a field of view having a first area onto which the marker configuration is imaged along a direct ray and at least a second area in which the marker configuration is imaged along at least one ray that is reflected by the mirror.

2. The system according to claim 1, characterized in that the X-ray phantom is detachably and reproducibly mounted in an accurate position by means of a mount on the acquisition unit of the position detection system.

3. The system according to claim 1, characterized in that the X-ray phantom is integrated into the acquisition unit of the position detection system.

4. A method of calibrating an X-ray diagnostic system, the method comprising:

providing a position detection system for detecting a marker configuration, the position detection system comprising an acquisition unit and an X-ray phantom disposed on the acquisition unit;

positioning the acquisition unit in a path of rays of the X-ray diagnostic system in a first projection geometry so that at least a portion of the X-ray phantom is projected onto an X-ray beam receiver by an X-ray source and so that the marker configuration can be detected by the position detection system;

acquiring a first 2D X-ray projection of the X-ray phantom and determining a position of the marker configuration with the position detection system in the first projection geometry;

acquiring a second 2D X-ray projection of the X-ray phantom in at least a second projection geometry and performing a 3D reconstruction of the X-ray phantom; and calculating a coordinate transformation between coordinate systems of the X-ray phantom and the X-ray diagnostic system based at least in part on the detected position of the X-ray phantom relative to the marker configuration and the position of the projection image of the X-ray phantom in the reconstructed volume relative to the marker configuration.

* * * * *